United States Patent [19]

Spitznas et al.

[11] Patent Number: 4,856,872
[45] Date of Patent: Aug. 15, 1989

[54] ATTACHMENT FOR MICROSCOPES

[75] Inventors: M. Spitznas, Bonn; Wolfgang Veit, Solms-Burgsolms; Rainer Kirchhuebel, Asslar, all of Fed. Rep. of Germany

[73] Assignee: Oculus Optikgeraete GmbH, Wetzlar, Fed. Rep. of Germany

[21] Appl. No.: 25,111

[22] Filed: Mar. 12, 1987

[30] Foreign Application Priority Data

Mar. 14, 1986 [DE] Fed. Rep. of Germany ....... 3608515

[51] Int. Cl.$^4$ ............................................. G02B 7/02
[52] U.S. Cl. ................................. 350/255; 350/429; 350/518; 351/205; 384/527
[58] Field of Search ............... 350/255, 251, 252, 429, 350/253, 515, 516, 518, 521, 556; 285/26, 32, 33, 39, 84, 86, 315, 331, 397, 398; 427/11, 231, 369; 351/205; 415/200, 212 A; 384/527

[56] References Cited

U.S. PATENT DOCUMENTS

| | | | |
|---|---|---|---|
| 1,755,759 | 4/1930 | Ahmels et al. | 350/518 |
| 3,168,610 | 2/1965 | Kende | 350/429 |
| 4,172,634 | 10/1979 | Thompson | 350/429 |
| 4,223,963 | 9/1980 | Glodin et al. | 384/527 |
| 4,326,789 | 4/1982 | Aoyagi et al. | 350/255 |
| 4,371,312 | 2/1983 | Tank | 415/212 A |
| 4,582,350 | 4/1986 | Okajima | 350/429 |
| 4,606,618 | 8/1986 | Geller | 350/556 |

*Primary Examiner*—Rodney B. Bovernick
*Assistant Examiner*—Loha Ben
*Attorney, Agent, or Firm*—Flynn, Theil, Boutell & Tanis

[57] ABSTRACT

An attachment for microscopes, in particular for stereomicroscopes, facilitates a contact-free viewing of an eye freely movable by the patient, in particular the fundus of the eye. Such an attachment must be easily and quickly attachable to the microscope and must deliver an image section of up to 120°. Moreover, the free movability of the eye must be assured and the attachment must also at high temperature be able to be sterilized quickly, without influencing the wearability of the attachment. This is achieved by an attachment having two lenses or lens systems, the distance between the systems being adjustable and the systems replacing the objective lens of the microscope. The housing of the attachment can be connected to the microscope through a screw or bayonetlike coupling. The outer lens of the attachment is arranged easily movably in axial direction relative to the housing, whereby all reciprocally movable and turnable parts of the attachment are provided with a coating, which consists of pressed and sintered PTFE polymers containing Al$_2$O$_3$ particles.

10 Claims, 2 Drawing Sheets

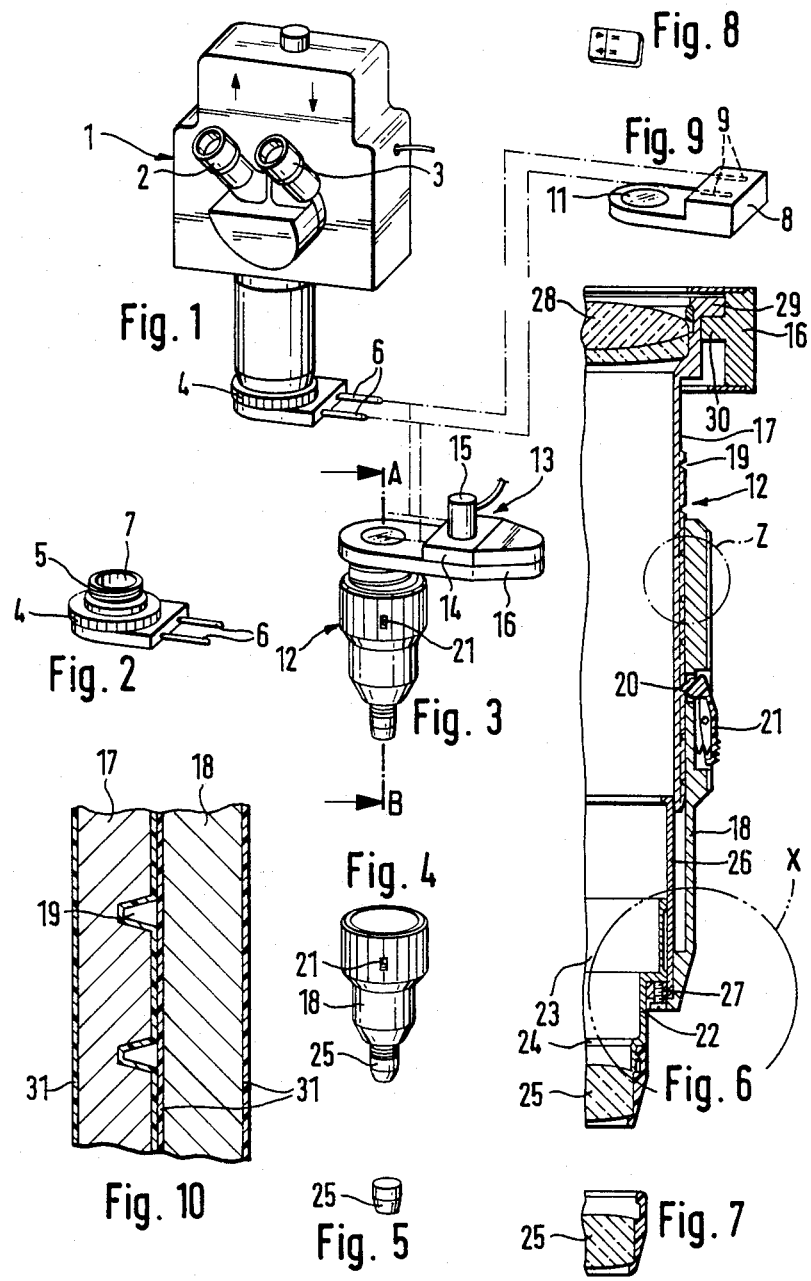

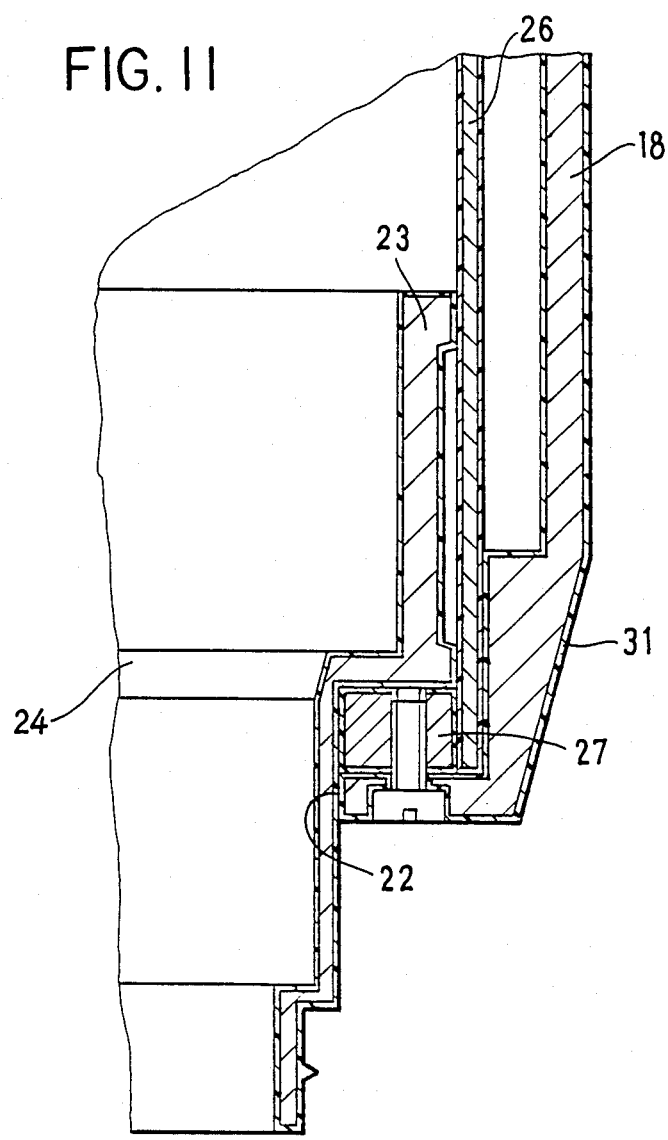

4,856,872

ATTACHMENT FOR MICROSCOPES

FIELD OF THE INVENTION

The invention relates to an attachment for microscopes, in particular for stereomicroscopes for facilitating a contact-free viewing of a freely movable eye of a patient, in particular the fundus of the eye.

BACKGROUND OF THE INVENTION

It is known to place a contact lens onto the eye to view the fundus of the eye. The contact lens makes it possible to view image sections of up to 20° on the fundus. Furthermore, a so called "Panfunduscope" is known, which enables a view of up to 150° of the fundus. However, a disadvantage of this known panfunduscope is that it requires a placement directly onto the eye. This makes complicated resetting operations necessary during surgeries, which must be carried out both in front of the eye lens and also behind the eye lens, so that both surgeries can be carried out with one surgery stereomicroscope. When using only one contact lens, this is avoided, however, the obtained 20° image section is relatively small, so that the microscope must often be reset, which is also disadvantgeous during such surgeries.

The basic purpose of the invention is to provide an attachment for microscopes, in particular for stereomicroscopes for facilitating a contact-free viewing of the abovementioned type, which can be attached easily and quickly to the microscope or to the stereomicroscope and which delivers an image section of up to 120° and permits a free movability of the eye and which most importantly can be quickly sterilized at high temperatures, without influencing the wearability of the attachment.

Thus the attachment consists according to the invention of two lenses or lens systems, the distance between which can be adjusted for the purpose of compensating for the sight deficiency of an eye of the patient- and which can be connected to the stereomicroscope through a screw or bayonet coupling. The two lenses of the attachment replace the lens of the stereomicroscope. The outer lens, that is the lens, which is opposed to the eye of the patient to be operated on, can be moved easily in axial direction of the attachment, so that also during an unintended movement of the eye by the patient, the lens gives way or yields and thus the eye cannot suffer damage. All reciprocally movable parts of the attachment are provided with a coating consisting of pressed and sintered PTFE polymers containing $Al_2O_3$ particles.

The attachment can thus be easily inserted into existing surgery microscopes and is advantageously provided with a quick-change mechanism, with which selectively the present objective of the stereomicroscope or, however, the attachment can be swung into the beam path of the stereomicroscope. This makes it possible to create an image of the front eye section through the normal objective and during a swinging over to the contact-free wide-angle system of the fundus of the eye. The system is optically tuned such that during this back and forth swinging, a sharp image is obtained both on the front and also on the rear eye section without any adjustment, if the patient is ametropic. For nonametropic patients, the upper system for the wide-angle viewing is constructed adjustably, so that a suitable refocussing can take place.

The lower adjustable system is according to the invention provided with a thread, into which a safety mechanism engages, which prevents a complete removal or disengagement, which can lead to accidents. The inventively suggested coating of the attachment has a temperature stability of up to 250° C., so that the complete system can be sterilized easily at least at 160° C. This coating has moreover the advantage that the mechanical antifriction properties are not lost during sterilization, so that an easy sliding of the parts in one another and also the movability of the outer lens in axial direction of the attachment is maintained without any interference even after several sterilizations. Fats and lubricants, as they are needed otherwise to obtain the easy motion between the individual parts, are not needed here.

The outer lens is constructed preferably completely exchangeably, so that here lenses for variable focuses can be used, so that differently large image sections can be obtained.

According to a preferable embodiment, the image changer, in which both the attachment and also the normal objective lens of the microscope are arranged, is provided with a motor, so that a quick change between both optical systems is possible.

It is common in some hospitals to hang a sterile plastic sack over the complete microscope, which is usually placed onto the objective lens attachment. This plastic sack can also be used with the wide-angle attachment through a changed adaptor. In addition, it is possible to moe from below a sterile plastic part onto the attachment, so that the sterility of the entire system is maintained.

BRIEF DESCRIPTION OF THE DRAWINGS

One exemplary embodiment of the invention will be described in greater detail hereinafter with reference to the drawing, in which:

FIG. 1 is a perspective view of a stereo surgery microscope with attached adapter;

FIG. 2 is a perspective view of the adapter;

FIG. 3 is a perspective view of a quick-change adapter with an attachment according to the invention;

FIG. 4 illustrates the lower part of the quickchange adapter according to FIG. 3;

FIG. 5 illustrates the outer, exchangeable lens of the attachment;

FIG. 6 is a cross-sectional view taken along the line A-B of FIG. 3;

FIG. 7 is a cross sectional view of the exchangeable outer lens;

FIG. 8 illustrates a control element for the change adapter according to FIG. 3;

FIG. 9 illustrates an attachment piece for connection to the adapter with the normal objective lens of the microscope;

FIG. 10 is an enlarged illustration of a portion Z of FIG. 6; and

FIG. 11 is an enlarged illustration of a portion X of FIG. 6.

DETAILED DESCRIPTION

FIG. 1 illustrates the stereomicroscope which is identified in its entirety by the reference numeral 1. The stereomicroscope consists of two eyepieces 2, 3 with their Porro prisms and the lens system and the magnification changer, both not illustrated in detail. An adapter 4 is inserted in place of the usual objective lens at the lower end of the microscope 1. The adapter has, as shown in FIG. 2, a threaded part 5 and two connecting pegs 6 and a center bore 7.

If the microscope 1 is to be utilized as a normal stereomicroscope, the fitting piece 8 according to FIG. 8 is moved to the adapter 4. The fitting piece 8 has two bores 9 into which the connecting pegs 6 of the adapter 4 are received. The objective lens 11 is inserted into the fitting piece 8 and lies, with the fitting piece attached, in the optical axis of the microscope.

The attachment 12 can be secured either to a like fitting piece 8, as this is illustrated in FIG. 9, or, however, to a quick-change adapter 13 according to FIG. 3. The quick-change adapter 13 has a fitting piece 14 with bores, into which the connecting pegs 6 of the adapter 4 are received. A motor 15 is furthermore secured to the fitting piece 14. A lever 16 is fixedly secured to the axle or shaft of the motor 15. The attachment 12 is arranged on one side of the lever 16 and the objective lens 11 is arranged on the other side and at the same distance or location as the attachment 12 on the lever 16. Thus, this quick-change adapter makes it possible to choose in a simple manner between the attachment 12 and the normal objective lens 11.

FIG. 6 is a side view of the attachment 12. The atachment 12 consists of two housing parts 17 and 18 which are screwed together. An acme thread 19 is for this purpose constructed on the outside of the housing part 17. A nose 20 of a safety mechanism 21 engages the acme thread 19. The acme thread 19 is constructed such that the housing part 18 cannot be completely removed from the housing part 17. The housing part 18 has a lower opening 22, into which a guide part 23 is received. The guide part 23 has a fastening mechanism 24 for an outer lens 25 of the attachment 12. The guide part 23 is movably arranged in axial direction in a guideway 26 fixedly connected to the housing part 18. If pressure is applied to the outer lens 25, the guide part 23 slides into the guideway 26 such that, in case the patient hits the outer lens 25 with his eye, damages to the outer lens and the patient's eye will not occur.

A ring 27 screwed to the housing part 18 is used as a lower stop for the guide part 23.

The inner lens system 28 of the attachment 12 is arranged in the upper end of the housing part 17. The end of the housing has a flange 29 resting on a shoulder 30 of the lever 16.

As shown in FIGS. 10 and 11, all reciprocally movable parts such as the parts 17, 18, 23 and 26, also the acme thread 19, are coated with a layer 31 consisting of pressed and sintered PTFE polymers containing $Al_2O_3$ particles which, because of $Al_2O_3$ particles have a high hardness, namely, a hardness of approximately 500 mHV, is obtained as a mixed hardness layer. The coating 31 has a very good abrasive resistance and very good antifriction properties, with the friction coefficient lying at $0.12\mu$ in dry conditions. Moreover, the coating is corrosion-resistant compared with most media, which lie in the pH-range between 3 and 9. This coating does not require any additional lubricants and has good temperature stability which is decisive for the attachment being able to be sterilized simply and quickly at temperatures above 160°. The good antifriction properties of the coating are not lost thereby. Only this coating makes the utilization in a stereo surgery microscope possible, because when using fats and lubricants a high-temperature sterilization would not be possible, since the fats would be driven out and sooner or later the necessary easy motion would no longer be assured.

The embodiments of the invention in which an exclusive property or privilege is claimed are defined as follows:

1. In a sterilizable attachment for a microscope, in particular stereomicroscopes for facilitating a contact-free viewing of an eye freely movable by the patient, in particular the fundus of the eye, the improvement wherein the sterilizable attachment has two lens means arranged in a housing thereof, the distance between said lens means being adjustable for the purpose of compensating for the sight deficiency of said eye, said lens means replacing the objective lens of the microscope, wherein said attachment having an adapter is connected to the microscope, an outer lens of said lens means being adapted to be positioned very close to a patient's eye, said lens means including support means for supporting said outer lens for easy movement relative to said housing in the axial direction thereof to prevent injury to said eye should the microscope be inadvertently adjusted or the patient's eye is inadvertently moved in such a manner to bring the lens into engagement with said eye, and wherein all reciprocally movable and turnable parts of said attachment are provided with a coating which consists of pressed and sintered PTFE polymers containing $Al_2O_3$ particles to facilitate them being sterilized in a heated environment without the heat causing a destruction of the ability of said support means allowing said outer lens to easily move relative to said housing.

2. The attachment according claim 1, wherein said housing consists of two housing parts which are screwed to each other and which have a safety mechanism for preventing an unintended separation thereof.

3. The attachment according to claim 2, wherein said safety mechanism consists of a spring-loaded nose, which is supported in a first housing part and engages an acme thread constructed on a second housing part.

4. The attachment according to claim 3, wherein said support means for said outer lens includes a guide part movable in a guide way in said axial direction, said guide way being fixedly arranged in said first housing part.

5. The attachment according to claim 4, wherein a work position of said outer lens is determined by a stop inserted into said first housing part.

6. The attachment according to claim 5, wherein said stop is formed of a ring.

7. The attachment according to claim 2, wherein said safety mechanism is a threaded nut.

8. In an attachment for a microscope, in particular stereomicroscopes for facilitating a contact-free viewing of an eye freely movable by the patient, in particular the fundus of the eye, the improvement wherein the attachment has two lens means arranged in a housing thereof, the distance between said lens means being adjustable for the purpose of compensating for the sight deficiency of said eye, said lens means replacing the objective lens of the microscope, wherein said attachment having an adapter is connected to the microscope, wherein a quick-change adapter is adapted to be attached to said adapter, which quick-change adapter has an axis of rotation to which a lever is secured, on which lever, at an equal distance from the axis of rotation, is arranged, on one side, said attachment, and on the other side, said normal objective lens of said microscope, wherein an outer lens of said lens means of said attachment is arranged easily movably relative to said housing in the axial direction thereof to prevent injury to said eye should the microscope be inadvertently adjusted to bring the lens into engagement with said eye, and wherein all reciprocally movable and turnable parts of said attachment are provided with a coating which consists of pressed and sintered PTFE polymers containing $Al_2O_3$ particles.

9. The attachment according to claim 8, wherein said quick-change adapter is connected to said adapter by connecting pegs of said adapter.

10. The attachment according to claim 8, wherein said axis of rotation of said quick-change adapter is coupled to a drive motor.

* * * * *